US007448376B2

(12) United States Patent
Lepel (10) Patent No.: US 7,448,376 B2
(45) Date of Patent: Nov. 11, 2008

(54) MEDICATION DELIVERY DEVICE AND METHOD

(76) Inventor: Pamela Lepel, 1382 Castle Rock Ct., DePere, WI (US) 54115

( * ) Notice: Subject to any disclaimer, the term of this patent is extended or adjusted under 35 U.S.C. 154(b) by 210 days.

(21) Appl. No.: 11/212,448

(22) Filed: Aug. 27, 2005

(65) Prior Publication Data

US 2007/0049841 A1 Mar. 1, 2007

(51) Int. Cl.
*A61M 11/00* (2006.01)
(52) U.S. Cl. ............... 128/200.14; 128/200.21; 128/200.23; 128/204.14; 128/206.21; 128/203.26; 128/203.27; 128/912
(58) Field of Classification Search ............ 128/200.14, 128/200.21, 204.14, 206.21, 203.26, 203.27, 128/912
See application file for complete search history.

(56) References Cited

U.S. PATENT DOCUMENTS

| | | | | |
|---|---|---|---|---|
| 3,221,733 | A | * 12/1965 | Beasley | 128/200.14 |
| 3,769,973 | A | * 11/1973 | Esbenshade, Jr. | 128/200.14 |
| 4,020,834 | A | 5/1977 | Bird | |
| 5,287,849 | A | 2/1994 | Piper et al. | |
| 5,357,945 | A | * 10/1994 | Messina | 128/200.14 |
| 5,704,344 | A | * 1/1998 | Cole | 128/200.14 |
| 6,698,426 | B1 | * 3/2004 | Wright | 128/204.11 |
| 6,805,118 | B2 | 10/2004 | Brooker et al. | |

OTHER PUBLICATIONS

Keith Wesley, MD, Mask CPAP for the EMT-Basic, in EMS Professionals, May-Jun. 2003, Http://www.wisconsinems.com/docs/CPAP.htm.
Paramedic Jan. 2003, p. 3B, Pulmonary Edema.
Paramedic Jan. 2003, p. 3C, CPAP.
Use of CPAP and BiPAP in Acute Respiratory Failure, pp. 1-2, author unknown, obtained at Http://www.theberries.ns.ca/Archives/CPAP.html.

* cited by examiner

*Primary Examiner*—Patricia Bianco
*Assistant Examiner*—Nihir Patel
(74) *Attorney, Agent, or Firm*—Allen H. Erickson

(57) ABSTRACT

A medication delivery apparatus and method for a continuous positive airway pressure (CPAP) system such as used in emergency treatment of severe respiratory distress. The apparatus of the invention includes a 3-port Tee fitting, one port of which is connected to the inlet port of a CPAP full face mask operable at a continuous elevated pressure. A second port is connected to a CPAP gas conduit supplying a pressurized oxygen-containing gas. The third port is connected to a flexible tube receiving aerosolized medication from an upper outlet of an openable/refillable lightweight nebulizer. The flexible tube is of a length to support a nebulizer in a vertical attitude.

15 Claims, 5 Drawing Sheets

MEDICATION DELIVERY DEVICE AND METHOD

BACKGROUND OF THE INVENTION

1. Field of the Invention

The present invention relates to a device and method for injecting a medication into a pressurized pulmonary respiration system. More particularly, the invention relates to a medication delivery device and method for pulmonary dosing in a Continuous Positive Airway Pressure (CPAP) system.

2. Background of Related Art

Many respiratory conditions and diseases exist which are treatable by the administration of oxygen or oxygen-enhanced air. Several examples of such are Chronic Obstructive Pulmonary disease (COPD), congestive heart failure (CHF), and asthma. Asthma is sometimes categorized as a COPD.

Chronic Obstructive Pulmonary disease (COPD) is a condition in which a patient's lung has limited elastic recoil and/or the alveoli and terminal bronchioles have stiffened with scar tissue. The terminal bronchioles may collapse during exhalation, leading to air trapped in the alveoli. The disease causes much discomfort inasmuch as a patient must work hard to breathe, and physical exercise is difficult.

Congestive heart failure (CHF) may result in "preload" in which the blood sent to the left ventricle by the lungs exceeds the heart's capacity. Alternatively, the pressure against which the heart is pumping may be excessive, a condition called "afterload". As a result of either or both conditions, a patient will lose the ability to absorb oxygen and get rid of carbon dioxide.

In any of the pulmonary diseases and conditions, a loss of oxygenation may reach a critical state requiring emergency treatment. Typically, emergency treatment must begin without delay, and equipment and medicinals for administering treatment are normally available in an emergency vehicle such as an ambulance. Depending upon the particular disease and condition of the patient, one or both of oxygenation and medication are commonly applied.

Other relatively common respiratory conditions exist, including for example, apnea, in which a patient has an absence of breathing. When it occurs during sleep, the condition may be fatal.

In addition to specific medicinal treatments, emergency treatment of respiratory distresses may include one or more of resuscitation, opening of an airway blockage for ventilation, and oxygen enhancement via nasal catheter, mask or endotracheal catheter. More complex systems are capable of increasing ventilation and oxygenation of a patient during the inhalation portion of the breathing cycle, but because of their complexity are not generally made available to emergency medical technicians (EMT's). An example of such a system is a Bi-level Positive Airway Pressure (BiPAP) system, in which a respiration machine senses the onset of a patient's inhalation cycle and elevates the pressure in the patient's airway for enhanced inhalation. The exhalation pressure is typically reduced.

The numbers of medical personnel in an ambulance is typically very limited, and the purpose is to transport a patient to a permanent medical facility quickly, performing only basic medical procedures required to protect the patient's life. Even a relatively minor invasive procedure such as ericothyriodotomy is not performed in a pre-hospital setting unless absolutely necessary to the life of the patient. Typically, such a procedure is an advanced skill performed by a medical doctor, flight nurse, or paramedic. This is not a skill performed by an emergency medical technician (EMT), as governed by standards of the profession. Currently, endotracheal intubation is indicated when a patient cannot oxygenate himself adequately, the "gag" reflex is gone, or a patient's breathing has stopped. In endotracheal intubation, a patient's airway is visualized, and a tube is inserted. Breathing is then taken over by manual assistance or mechanical ventilator. Hazards associated with endotracheal intubation include hypoxia, aspiration, trauma to the airway, and an acquired dependency of the patient to the ventilator. Therefore, intubation is generally not performed unless absolutely necessary.

In the practice of respiratory treatments, available face masks are designed to provide oxygen/air through the mouth and nostrils of a patient, and assume that in the event a nebulized medication is to be administered, the patient's head and upper body will be raised i.e. substantially upright. Thus, the centerline axis of the mask's inhalation port is substantially parallel to the patient's longitudinal axis, i.e. nearly horizontal when the patient is in a supine position. A nebulizer's outlet is constructed to fit rigidly into the mask's inhalation port, and a patient is supported in an upright position during the administration. However, in an emergency situation in which the patient's condition (severe injury/illness) requires a supine position, a way must be found to administer a nebulized medication at a controllable rate and without undue stress to the patient. Attempts to administer a medication aerosol to a face mask of a supine patient may result in non-delivery and wastage of a substantial portion of the medication due to flooding of the nebulizer. The un-aerosolized medication may be carried over into the mask and discharged. Thus, a patient is deprived of much of the medication.

In emergency medical pre-hospital situations, time is usually a critical factor. Typically, emergency i.e. pre-hospital personnel make a rapid diagnosis to determine what procedures are required to maintain life and prevent patient deterioration during transit to a treatment center, e.g. hospital. Emergency personnel must determine whether respiratory treatment is indicated, and if so, whether the indicated treatment is to be minimal, such as the simple application of a stream of oxygen or oxygen-enriched air (e.g. such as 21-90 percent oxygen) by mask or nasal cannula, or when a more invasive technique requiring endotracheal intubation is indicated.

In most breathing emergencies, a variety of medications such as bronchiodilaters (e.g. albuterol) may be indicated, depending upon the diagnosis protocol. Providing oxygen through an endotracheal catheter has a number of disadvantages relating to simultaneous or co-medication of the patient. In order to apply an aerosolized medication, the endotracheal tube may be removed from a ventilatory source to inject the desired medication. Often, multiple doses of more than one type of medication may be required, leading to less than optimal ventilation/oxygenation as well as irritation of the patient's throat. In some emergency situations, continuous application of both oxygen and medicinals may be indicated, in which case the emergency personnel must attempt to provide both oxygen and medicinals with minimal downtime for each. In some cases, adequate oxygenation/respiration and adequate medication delivery cannot be both maintained, leading to extreme stress to the patient, and deterioration of the patient's condition.

In the past few years, another technique has been developed which is intermediate simple oxygenation and the more radical procedures requiring endotracheal intubation. The method has been used for many years in some fixed installations (e.g. hospital emergency rooms) but not generally in emergency vehicles. This method is known as Continuous Positive Airway Pressure (CPAP) and is appropriate for patients suffering severe respiratory distress for which normal oxygenation/respiration at atmospheric pressure is less than effective. Prior to the availability of emergency CPAP treatment, the patient was typically subjected to endotracheal intubation, a much more invasive procedure. A current protocol for the use of CPAP is summarized in a reference in PARAMEDIC 01/03, page 3C entitled CPAP.

Figures 1, 2A:
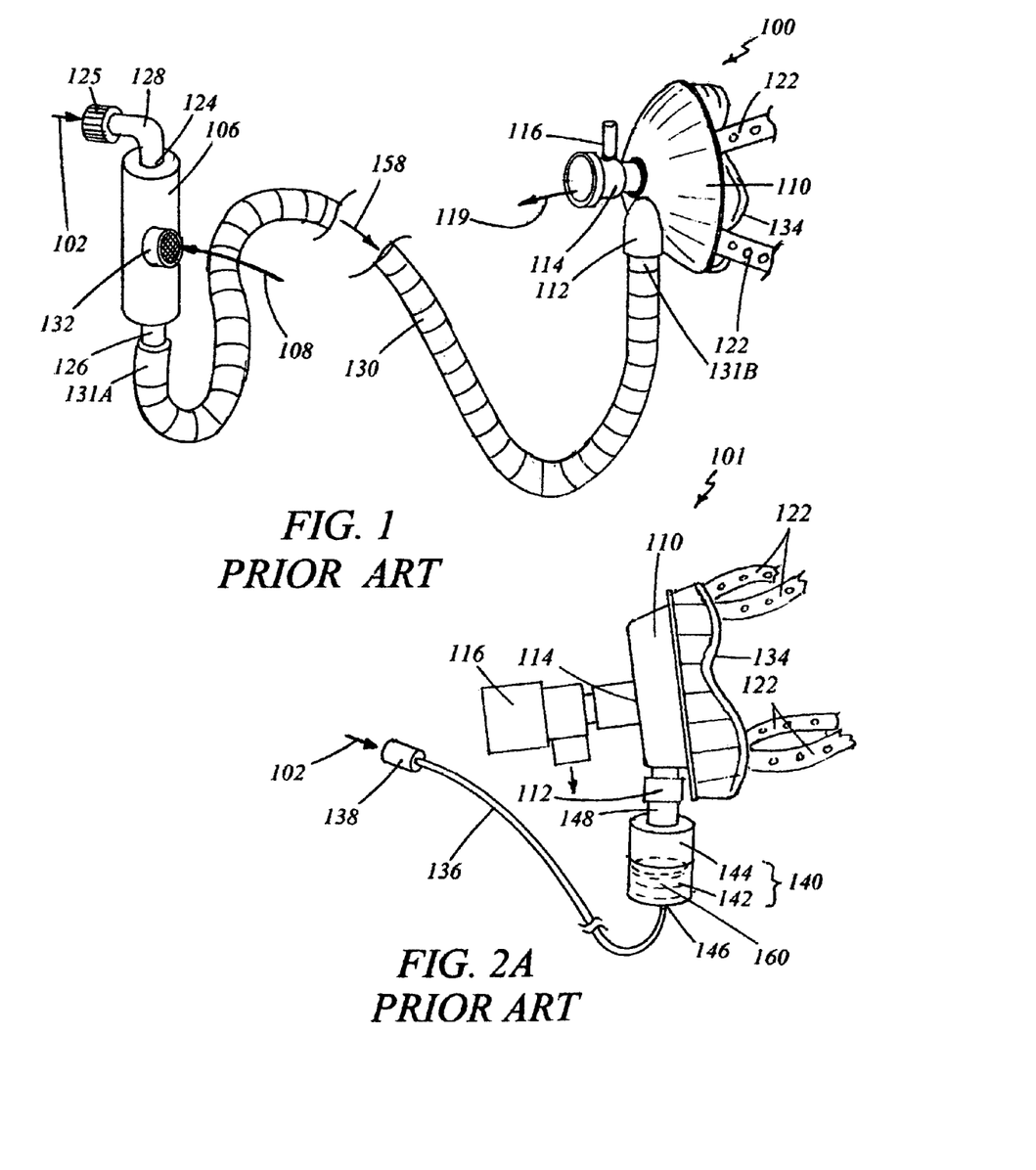
FIG. 1 is a generalized perspective view of a PRIOR ART exemplary continuous positive airway pressure (CPAP) system to which the present invention is directed.
FIG. 2A is a perspective view of a PRIOR ART apparatus for administering a medicinal aerosol into a CPAP mask wherein shutdown of the CPAP oxygen flow is required during medicinal administration.

In the CPAP method, a continuous positive internal pressure is applied to the patient's airway during both inhalation and exhalation. As shown in FIG. 1 of the drawings, a simple CPAP apparatus 100 of the prior art includes an oxygen source 102 capable of delivering a pressurized stream of oxygen 104 or oxygen diluted to a lower concentration, such as for example 25-90 percent. A gas diluting apparatus 106 may be used to dilute a nearly pure oxygen stream 104 with filtered atmospheric air 108 to a desired concentration using aspiration, thus reducing the weight of pressurized gas which must be carried aboard an emergency vehicle. A tightly-fitting mask 110 is required to prevent undue leakage at the mask-face interface 134, and to maintain a desired airway pressure. The CPAP face mask 110 has an inhalation port 112 and an exhalation port 114, the latter having a Positive End-Expiratory Pressure (PEEP) valve 116 which maintains a positive pressure in the mask and patient's airway. Often, a filter is incorporated into the PEEP valve 116 to prevent escape of exhaled fluids, etc. into the atmosphere. The maintained pressure is typically between about 5 cm. water and about 15 cm. water but may be higher or lower, for example, from about 2 cm. water to about 30 cm. water, or even higher, depending upon the pressure requirement for maintaining the airway of the patient in an open condition. This pressure offsets (at least partially) the pressure against which the patient must work to inhale, and maintains an open airway in exhalation. In COPD patients, the enhanced pressure prevents collapse of the terminal bronchioles, enhancing the exchange of oxygen and carbon dioxide. In a patient experiencing congestive heart failure (CHF), the enhanced constant pressure decreases myocardial workload while nitroglycerin is administered to dilate the arteries. Arterial dilation reduces both preload and afterload on the heart.

A Continuous Positive Airway Pressure (CPAP) treatment protocol is being considered for widespread use by emergency vehicle EMT-rated personnel, inasmuch as this method may avoid the use of invasive endotracheal intubation by endotracheal catheter. In addition, the CPAP method is straight-forward, does not require complex equipment, and is relatively easy to pre-indicate, administer, and moniter. Although CPAP has been used in hospital settings for years, the method has now been very successfully tested in some emergency vehicle venues for administration by EMT-rated personnel. General information regarding the CPAP methods and proposed use in emergency vehicles is provided in Use of CPAP and BiPAP in Acute Respiratory Failure, pp. 1 and 2 (author unknown), found at http://www.theberries.ns.ca/archives/CPAP.html.

The administration of an aerosol medication while maintaining a CPAP positive pressure of air or oxygen-enhanced air in the patient's airway represents a drawback of the current CPAP method. Typically, to dose with a medicinal aerosol, the pressurized mask is temporarily removed, and medication administered by a hand-held nebulizer or through a nebulizer mask until the medication 160 in the nebulizer jar 142 is depleted, at which point the hand-held nebulizer is removed and the CPAP mask reattached and started for oxygenation/ventilation.

Optionally, the CPAP oxygen/air stream is disconnected from the CPAP face mask and replaced by a nebulizer outlet port. Thus, the aerosol is introduced during a time when gas pressure may be insufficient to keep the airway open, or the quantity of oxygen may be too low. As a result, much of the medication may be wasted. Furthermore, the period without positive pressure may significantly reduce ventilation/oxygenation, i.e. starving the patient of oxygen. Thus, a loss of positive pressure during the medication administration period may have serious consequences. In current practice, nebulisation of a single medication dose may take up to 3-4 minutes or longer.

In addition, this method requires the patient's head to be in an upright, i.e. erect position, as described in a protocol in PARAMEDIC 01/03 entitled Pulmonary Edema. This position may be difficult to attain or maintain, and tipping of the nebulizer container e.g. jar 142 from a vertical position may have deleterious medical consequences. If a patient's head is not kept upright (see prior art FIG. 3), the nebulizer (firmly attached to the mask) will be tipped from a normal vertical position, interrupting or reducing gas flow through the medication. Aerosolization of the medication will cease or become reduced. Furthermore, tipping of the nebulizer container 142 may allow the liquid medication to flow from the nebulizer outlet without being aerosolized.

Figure 3:
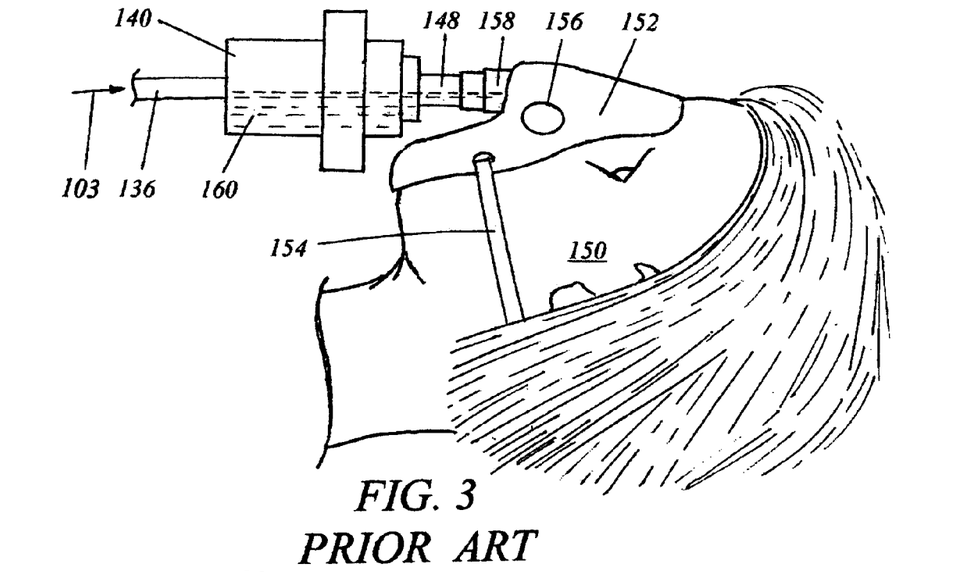
FIG. 3 is a perspective view of a PRIOR ART method for administering a medicinal aerosol into a conventional nebulizer face mask worn by a supine i.e. face-up patient.
Figure 4:
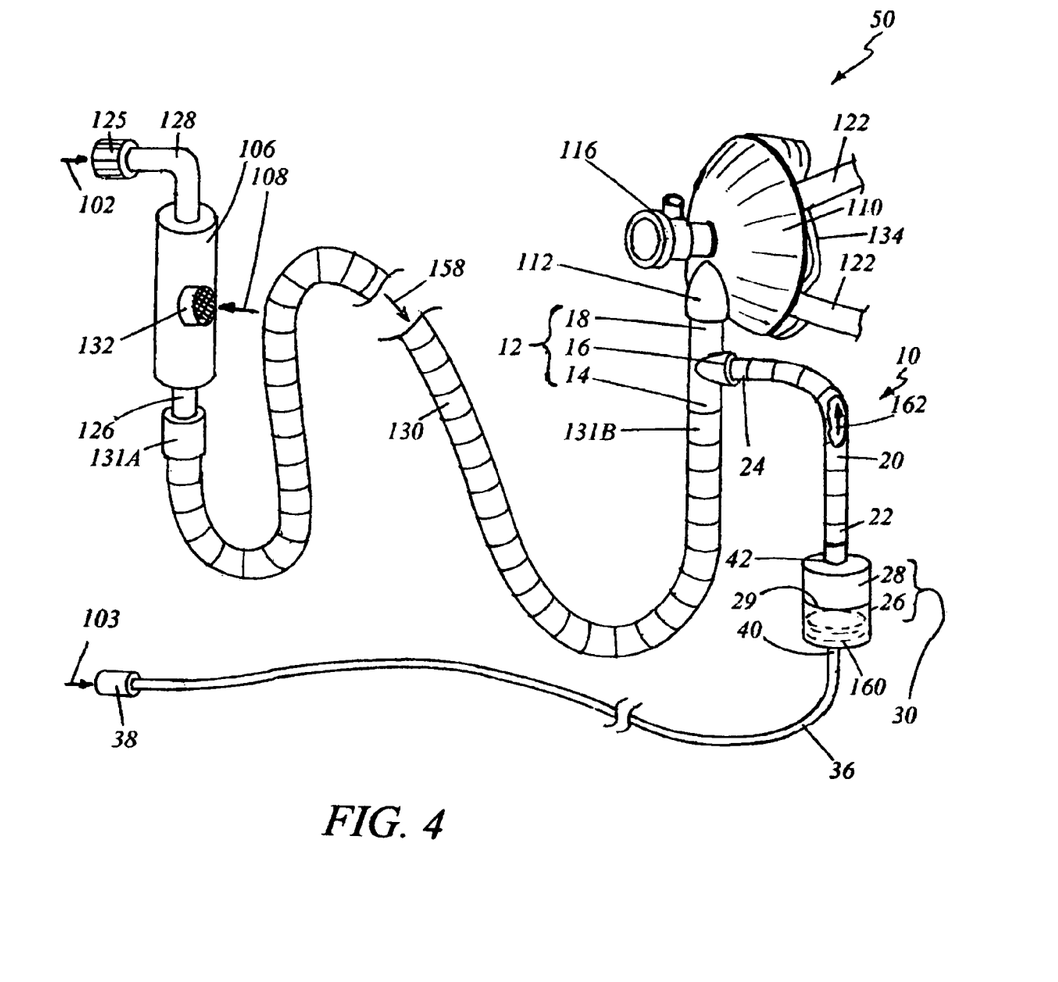
FIG. 4 is a perspective view of an exemplary CPAP apparatus to which a medication delivery device of the present invention is attached.

An improved procedure has been proposed by Keith Wesley, MD, in MASK CPAP FOR THE EMT-BASIC in EMS Professionals, May-June, 2003, pp. 1-3 whereby the nebulizer is positioned in-line with the bulk CPAP oxygen stream, using the oxygen stream to nebulize the medication, as depicted in Prior Art FIG. 3. However, this method prevents independent control of (a) the flowrate and pressure of the CPAP oxygen-enhanced stream and (b) the flowrate and nebulizer pressure drop of the nebulizing stream. This method may limit the total gas flow rate to the capacity of the nebulizer, which may be inadequate for proper CPAP operation. In addition, this method requires that the patient's head 150 must be positioned in a substantially upright position. Such is not always possible in a pre-hospital emergency situation because of injuries and/or illness, limited time, limited personnel, limited equipment, and/or for other reasons. As illustrated in FIG. 3, when the nebulizer cannot be maintained in a "top-side up" vertical position, liquid medication will not be aerosolized and may be largely wasted. The Wesley reference points out that in the recommended procedure, faster nebulization occurs, but "some of the medication condenses in the tubing or leaks out the PEEP valve".

U.S. Pat. No. 4,020,834 dated May 3, 1977 to Bird discloses a respiration apparatus for treating patients in a BiPAP manner, maintaining a positive pressure during exhalation and substantially atmospheric pressure during inhalation. The apparatus and its operation are very complex. The administration of medication in a Continuous Positive Airway Pressure (CPAP) apparatus is not in view.

U.S. Pat. No. 5,287,849 dated Feb. 22, 1994 to Piper et al. discloses a medicinal aerosol delivery system for a patient's lungs. The apparatus is directed to endotracheal use and is not meant for use in a CPAP operation.

U.S. Pat. No. 6,805,118 dated Oct. 19, 2004 to Brooker et al. describes a pulmonary dosing system and method in which a medication is administered in pulsed doses entrained in air. The administration to a patient continuously maintained at a positive pressure is not in view.

None of the cited prior art documents patents provide a method for administering a medication during CPAP respiration in which the patient's head is in a non-upright position. None of the cited art overcomes the problems presented by administration of a medicinal aerosol to a patient undergoing emergency CPAP therapy, such problems including patient stress resulting from excessive time without positive pressure, insufficient exposure to medication aerosol, dumping of the liquid medication into the mask or mouth, and other incidents which may likely occur.

Efforts to overcome the disadvantages of the prior art with respect to the administration of medications during emergency CPAP have led to the effective apparatus and methods of the invention which are herein described, illustrated and claimed, infra.

SUMMARY OF THE INVENTION

The present invention is apparatus and method for administering a medicinal aerosol to a patient undergoing Continuous Positive Airway Pressure (CPAP) respiration. The apparatus and method are typically applicable in what are considered emergency events.

In CPAP, a tight-fitting mask is used to eliminate or minimize leakage between the patient's face and the mask. The CPAP mask includes means for controlling the pressure in the mask at a constant or varying elevated pressure such as between 1 and 50 cm. water (above atmospheric pressure), so that the patient is forced to inhale with, and expire against the positive pressure. A source of oxygen or oxygen-containing gas (e.g. air) is provided at a pressure greater than the mask pressure to ensure that a desired oxygen concentration is continuously available to the patient's airway and lungs at a pressure which maintains an open airway.

In contrast to the prior art, a medication delivery device of the present invention includes a three-port Tee fitting, one port of which may be fitted into the inlet port of a CPAP mask. The bulk stream of oxygen-containing gas is connected to another port of the Tee fitting. A flexible corrugated tube connects the remaining port of the Tee fitting to the outlet of a medication nebulizer. In the nebulizer, a stream of pressurized gas, typically an oxygen-containing gas, aerosolizes a medication placed in the nebulizer container. The nebulized medication and gas passes through the flexible corrugated tubing (aerosol conduit) and is mixed with the CPAP oxygen/air stream and introduced into a CPAP mask maintained at an elevated pressure. The nebulizer has a supply of oxygen, air, or other gas which may be independent of the CPAP oxygen source. The gas supply stream to the nebulizer is controlled at a flow rate which provides a desired nebulization rate independently of the flowrate of the CPAP oxygen stream. The generated medication aerosol is directed from the nebulizer into the aerosol conduit. The aerosol conduit or delivery tube is of a sufficient length and flexibility such that the nebulizer may be positioned and maintained in an upright attitude irrespective of the attitude of the patient's head or CPAP mask. Preferably, the aerosol conduit is connected to the side port of the three-port Tee fitting, to position the nebulizer laterally from the patient's head. It is advantageous to provide an aerosol delivery tube with minimum length, to minimize condensation of aerosol in the cold tube. An aerosol delivery tube length of about 5-10 cm. is considered to be minimal for permitting a 90 degree bend downward from the horizontal, for an upright nebulizer. More generally, the length of the aerosol conduit may be about 4 cm. to about 50 cm., although even longer lengths may be necessary in some circumstances where the nebulizer cannot be placed any closer to the patient. In general, the tube length is preferably as short as possible within the constraints of available space and the necessity for the nebulizer to be upright and readily accessible.

In one embodiment of the medication delivery device, components generally available on an emergency ambulance vehicle may be assembled to provide the complete apparatus. For example, the medication delivery device may be formed by serial attachment of the following conventionally available components: (a) three-port Tee fitting, (b) medicinal delivery tube(aerosol conduit), (c) tube-to-nebulizer adapter, (d) nebulizer with medication container and gas inlet, and (e) nebulizing oxygen tubing connected to a pressurized oxygen source reduced to a desired nebulizing pressure, e.g. about 5-100 inches water. The nebulizing pressure is a function of the CPAP mask pressure, the nebulizer design (affecting pressure drop), and the nebulizing rate to be maintained. Typically, the oxygen source is a high pressure gas cylinder to which a pressure regulator is connected for maintaining a controlled outlet pressure at which the desired rate of aerosolization will occur.

In another embodiment of the invention, the device is formed as a unit and does not require adapters for connecting the various components. For example, the Tee fitting and medicinal tube may be formed as one piece, and the medicinal delivery tube (aerosol conduit) may be formed with an integral end configured to join with the nebulizer outlet. Thus, emptied nebulizers may be quickly removed and replaced by filled nebulizers (of the same or differing medication) in a few seconds.

In one embodiment, the Tee fitting is separable from the rest of the device, so that the delivery tube of the device may be connected directly to the inhalation port of a conventional nebulizer mask.

In one embodiment of the invention, the steps used in the method of the invention may be generally characterized as (a) providing a CPAP apparatus with an oxygen or oxygen/air supply conduit and a tightly fitting CPAP mask having an inlet port and an outlet port with a pressure controller capable of maintaining a continuous positive pressure in a patient's airway, (b) connecting a third port of a three-port Tee fitting to the CPAP mask inlet port (inhalation port); (c) connecting a second port of the three-port Tee fitting to the oxygen/air supply conduit, (d) providing a flexible aerosol delivery tube with inlet and outlet ends; (e) connecting one end of the aerosol delivery tube to the first port of the Tee fitting; (f) providing a medication nebulizer with a medication jar (container), oxygen inlet port and aerosol outlet port; and (g) connecting the other end of the aerosol delivery tube to the nebulizer outlet aerosol port. A combined flow of oxygen-containing gas and medication aerosol is then provided to the patient by (h) providing a pressurized oxygen-containing gas (via oxygen/air supply conduit) at a desired rate to the Tee fitting, (i) independently introducing a gas to the nebulizer oxygen inlet port at a desired rate to form and provide a medication aerosol to the Tee fitting, and (j) setting the PEEP on the outlet port of the mask to maintain a desired continuous positive pressure within the mask and patient's airway. It is understood that the order of the steps of the method may be varied as long as the apparatus as described is formed and then operated to provide a substantially continuous stream of oxygen-containing gas and aerosolized medication to a continuously pressurized mask.

It has been found that the nebulization rate is highly controllable, and higher rates are possible when compared to various methods of the prior art. When empty, the nebulizer container may be opened and refilled without shutting down the CPAP gas flow, or the CPAP gas flow may be shut down for a very brief period, such as for example, about 10 to about 20 seconds, to exchange a filled nebulizer container for the empty container. Thus, the administration of positive pressure oxygen-containing air (ventilation) and administration of medication aerosol are conducted substantially simultaneously rather than sequentially. Where a patient requires a medication (or medications) on a continuous basis, administration of the medication can be performed without significant suspension of the CPAP operation during either medication delivery or nebulizer refill.

All of the CPAP operations including medication delivery are generally within the scope of an EMT's duties, not requiring an attending physician or paramedic.

Other features and advantages of the present invention will become apparent to those of skill in the art through consideration of the ensuing detailed description, the accompanying drawings, and the appended claims. The drawings contain idealized representations for better illustration of the apparartus and methods of the invention, and various elements of the prior art are not necessarily shown, and dimensions may not be shown to scale.

BRIEF DESCRIPTION OF THE DRAWINGS

In the drawings, which depict exemplary embodiments of the prior art and various features of the present invention.

DETAILED DESCRIPTION

The present invention comprises an apparatus and method for administering a nebulized medication into a patient undergoing emergency oxygen therapy in which the patient's airway is continuously subjected to an elevated pressure during both inhalation and exhalation cycles. The oxygen therapy method is commonly known as Continuous Positive Airway Pressure (CPAP). In the past, it has been largely used in hospital settings. CPAP has now been approved in some states for use by Emergency Medical Technicians (EMT's) without the attendance of physicians or paramedics, such as in emergency vehicles (e.g. ambulances). The CPAP method provides an effective and advantageous alternative to invasive tracheotomy surgery and endotracheometric intubation. The method utilizes some of the same equipment used in simple mask oxygenation.

In CPAP, the face mask pressure of a patient is typically preset or adjusted within a broad range from about 1 cm. H2O to about 25 cm. H2O (or higher) above atmospheric pressure. In most cases, the airway pressure is controlled at between about 2.5 cm. H2O and 12.5 cm. H2O, which is sufficient to maintain the airway in an open condition. The concentration of oxygen in the incoming gas usually exceeds that of air, i.e. >21 percent, and normally may be in a range between about 25 percent and 99 percent oxygen.

A generalized prior art CPAP apparatus 100 exemplary of the current state of the art is shown in FIG. 1. The CPAP apparatus 100 includes an oxygen source 102 which provides oxygen at an elevated (i.e. positive) pressure and a controllable flowrate. The oxygen gas from source 102 may be supplied at a desired pressure and rate by what is commonly termed a respiration machine, not shown. The pressure of oxygen gas from the respiration machine is somewhat greater than the pressure at mask 110, to overcome the pressure drop through second conduit means 130. In some cases "pure" oxygen of about 90+ percent oxygen is diluted on-site to a desired lower concentration by atmospheric air.

FIG. 1 shows the major elements of a conventional PRIOR ART Constant Positive Airway Pressure (CPAP) apparatus 100 in simplified form. These elements include an oxygen source 102, a first conduit means connected to the oxygen source 102 by fitting 125, and first conduit means 128 connected to inlet port 124 of dilution device 106. Pressurized oxygen from source 102 is transported to dilution device 106, which may include an aspirator which draws in atmospheric air 108 through inlet 132 and filter 132A to dilute the "pure" oxygen. Diluted pressurized oxygen 158 then flows from outlet 126 through second conduit means 130 to the inlet i.e. inhalation port 112 of a tightly-fitting mask 110. The second conduit means 130 is typically formed of flexible (generally corrugated) plastic tubing with non-corrugated ends 131A and 131B. The CPAP mask 110 has an exhalation port 114 into which may be fitted a Positive End Expiratory Pressure (PEEP) valve 116 to maintain the desired airway pressure within the mask 110. The PEEP valve 116 may be limited to a single mask pressure such as 5 cm. water, or may be controllable at one of two or more pressure settings (e.g. 5, 7.5 and 10 cm. water. If desired, the actual pressure within the mask 110 may be monitored by means known in the art. CPAP mask 110 is shown with straps 122 for firm attachment to a patient's head 150C (see FIG. 3), thereby preventing significant gas leakage at the mask-to-face interface 134.

Figure 2:
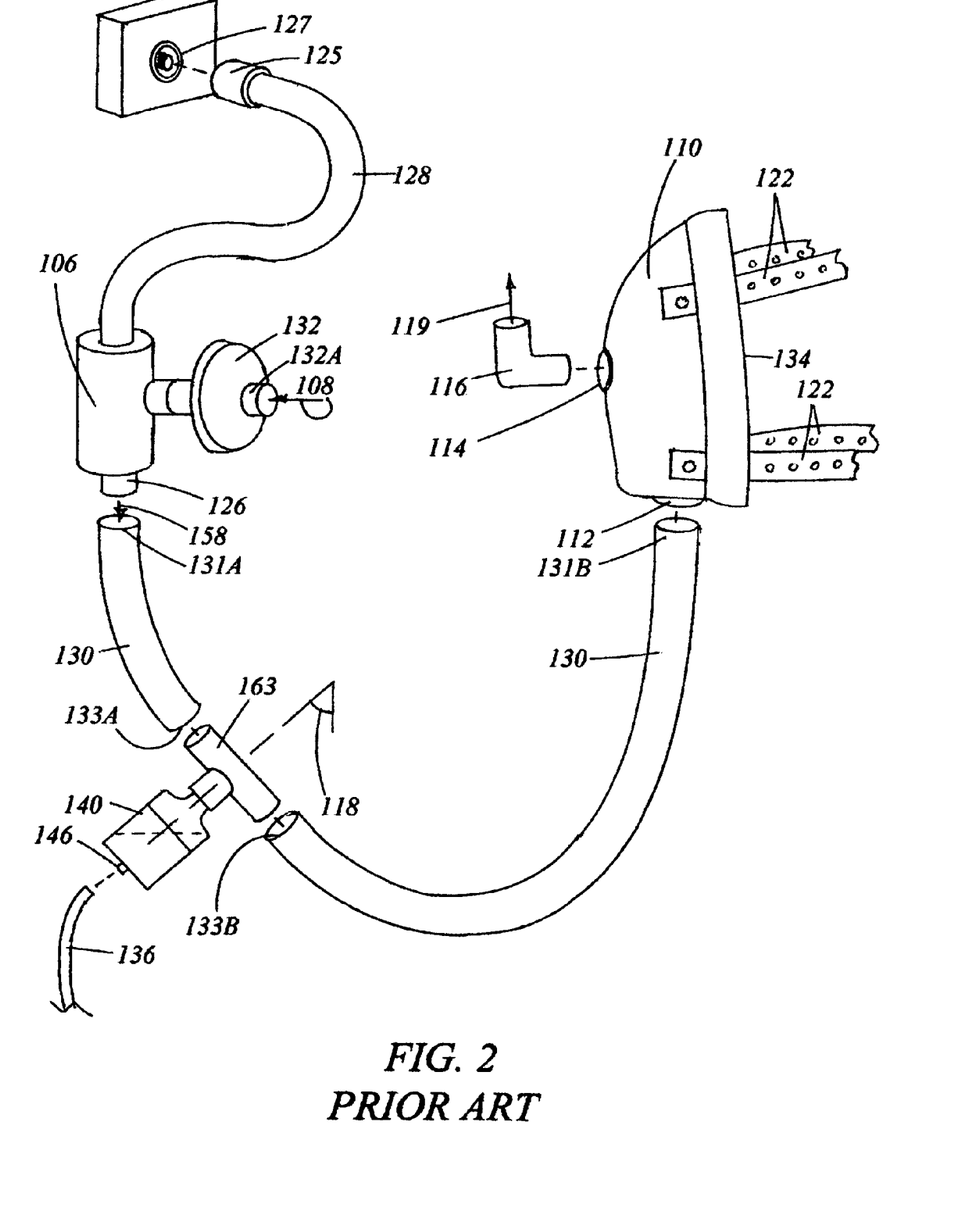
FIG. 2 is a perspective view of a PRIOR ART apparatus for administering a medicinal aerosol into a CPAP mask during oxygen administration.
Figures 5, 6:
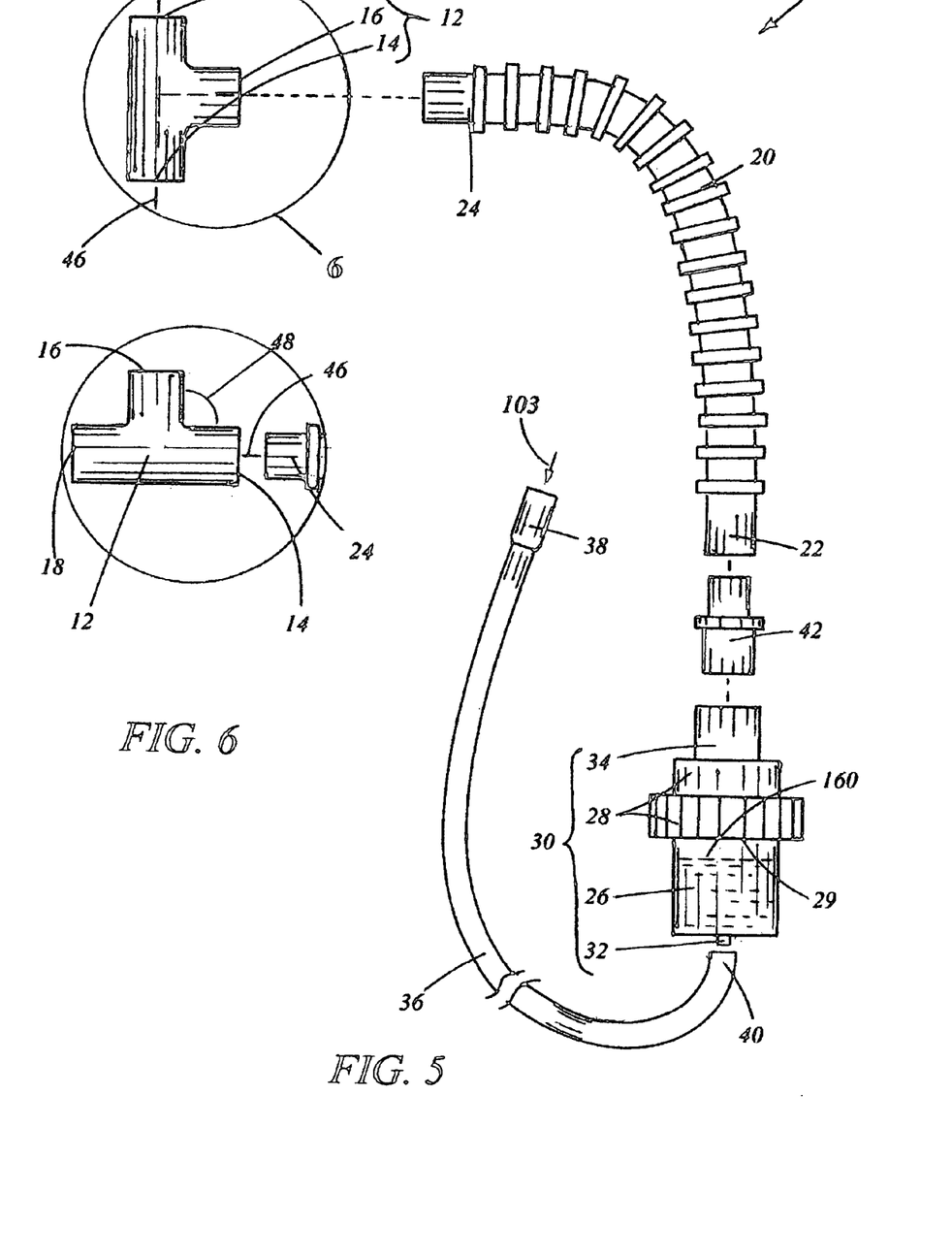
FIG. 5 is an exploded view of a medication delivery device in accordance with an embodiment of the present invention.
FIG. 6 is an exploded view of a circular portion 6 of FIG. 5, in which a connections to ports of a 3-port Tee fitting are varied in accordance with another embodiment of a medication delivery device of the invention.

FIG. 2 illustrates another PRIOR ART CPAP medication system 100 which is used in ambulance service. The CPAP system 100 is shown with an oxygen source comprising a wall outlet 127. First conduit means 128 has a connector 125 which sealingly fits into the wall outlet 127 for passage of oxygen to an oxygen dilution device 106. The dilution device 106 has an air inlet 132A for entrance of dilution air 108 through filter 132 The dilution device 106 is connected to a second conduit means 130 which typically comprises a substantial length of nominal 1-inch OD flexible corrugated plastic tubing. One end 131B of the conduit means 130 is connected to the inhalation (inlet) port 112 of a CPAP mask 110. For dosing with an aerosolized medicinal 162, the conduit means 130 is cut and two Tee ports of a Tee fitting 163 connected to the cut ends 133A, 133B. A nebulizer 140 is connected to a side Tee port of the Tee fitting 163. The nebulizer 140 is configured so that the oxygen/air flow 158 (i.e. the CPAP gas) is passed through the nebulizer 140 to aerosolize the medication. There are major disadvantages to this system, including the following:

(a) The conduit means 130 must be cut and both cut ends fitted to a Tee fitting 163, taking extra time in an emergency situation;
(b) The system requires that the nebulizer 140 be placed (or held) where it will not tip from an upright position, which in general is at some distance from the patient. Often, it requires a person to hold it in the proper orientation, particularly if the patient is fighting treatment. The long run of conduit means 130 results in considerable condensation of medication on the interior walls. Up to about one-half or more of the medication may condense and never enter the patients's airway;
(c) The optimum CPAP oxygen rate for a patient's respiration may differ widely from the optimum rate for achieving a desired nebulization rate of medication. An EMT may be required to determine some compromise, with resulting non-optimum treatment of the patient with respect to either or both of total oxygen supplied and nebulized medication supplied to the patient.

In FIG. 2A, a PRIOR ART medication dosing system 101 is shown which may be used with a CPAP apparatus. The system includes a nebulizer 140 having a medication jar 142 and cap 144. The nebulizer outlet 148 is rigidly held in inhalation port 112 of the CPAP mask 110. Oxygen and/or air from source 102 is fed through fitting 138 and inlet tubing 136 to the inlet port 146 of nebulizer 140, wherein the liquid medication 160 is so-called "vaporized" or "aerosolized" into an aerosol and delivered to the mask 110 for uptake by the patient. In general practice, the CPAP conduit means 130 is removed during the period of medication delivery, resulting in periods without the necessary oxygenation under pressure. The loss of CPAP oxygen flow may result in under-oxygenation of a patient. As already stated, the method is not effective unless it is possible to maintain the nebulizer 140 in an upright attitude where a major portion of the medication 160 will be nebulized. Furthermore, blockage of the airway because of loss of CPAP pressure will tend to prevent effective contact of medication aerosol with the patient's lungs.

In an alternative method, the CPAP mask is simply removed and replaced by a standard nebulizer facemask 152 for medication delivery, as shown in Prior Art FIG. 3. The airway pressure is lost during medication delivery.

In contrast to apparatus and methods of the prior art, the medication delivery device 10 and methods of the present invention, as depicted in FIGS. 4, 5, 6 and 7, solve various afore-mentioned problems associated with the methods and apparatus of the prior art.

First, use of the device of the invention permits the patient's head 150 to be in any position or attitude, without jeopardizing full delivery of the medication aerosol.

Second, the method of the invention produces co-delivery of the oxygen-containing CPAP gas and aerosol of the medication 160 during both of the inhalation and exhalation periods of a breathing cycle. It is not necessary to shut down the CPAP apparatus 100 for extended periods during medication delivery and/or nebulizer refilling/exchange.

Third, the pressures and flowrates of CPAP gas and medication delivery gas are separately controllable, making possible control of the medication rate from slow to very rapid.

Fourth, the device is simple and very lightweight. It takes up little space, whereby three units are generally storable in less than about 0.05 cubic foot. Thus, a number of the devices 10 may be easily placed and used on an emergency vehicle.

Fifth, the device is primarily intended for use with a CPAP apparatus at positive pressure. If necessary, however, it may also be simply used in combination with a nebulizer face mask 152, replacing use of a conventional nebulizer 30 which fits directly into the mask, particularly when the patient's head cannot be lifted to at least a somewhat upright position.

Sixth, the device and method of the invention are considered to be well within EMT protocol and easily used thereby, thus enabling inclusion in emergency vehicles, even in the absence of a physician or paramedic.

The apparatus of the invention comprises a medication delivery device 10 for concurrent/simultaneous use with emergency CPAP ventilation of a patient. As shown in FIG. 4, a conventional CPAP apparatus with attached medication delivery device 10 of the invention is designated herein as combined CPAP/medication delivery apparatus 50.

The medication delivery device 10 comprises a nebulizer 30 shown with a medication container 26 e.g. jar which is removable from nebulizer cap 28 along jar/cap interface 29 for placement of a liquid medication 160 therein. Typically, the container 26 is sealably attached to the cap 28 by screw threads or a compression (snap) fitting, not shown. The nebulizer 30 may be of any design or manufacture useful in medication nebulization, provided that it will assume an upright attitude for full nebulization when freely suspended from a medicinal aerosol delivery tube 20 attached to the first port 16 of Tee fitting 12. Oxygen and/or air is directed to nebulizer 30 from a gas source 102 through fitting 38 and gas supply tube 36, to nebulize the medication 160 to an aerosol 162. The gas source 102 may be the same source which supplies the CPAP unit 100, or may comprise a different source, e.g. a different oxygen cylinder. The oxygen/air supplied to the nebulizer 30 must be of a higher pressure than the oxygen/air supplied to the CPAP device, to compensate for the pressure drop across the nebulizing nozzle, not shown, within the nebulizer 30.

A medicinal aerosol delivery tube 20 has a first end 54 connected to the nebulizer outlet port 34 and a second end 56 connected to one port, preferably a side port 16, of a three port Tee fitting 12. Where conventional medical components are used to form a medication delivery device 10 of the invention, it may be necessary to insert a rigid adapter 42 between the gas port outlet 34 of the nebulizer 30 and the first end 54 of the delivery tube 20, if the sizes of outlet 34 and first end 54 are not compatible.

The three port Tee fitting 12 has a second port 14 which is connectable to the second end 131B of second conduit means 130, for flow of CPAP oxygen 158 therethrough. Third port 18 of Tee fitting 12 is configured to mate with the inhalation port 112 of the CPAP mask 110. As already indicated, first port 16 of Tee fitting 12 is connectable to the medicinal delivery tube 20.

When suspended from the short piece of delivery tube 20, the nebulizer remains in a vertical attitude for providing a continuous aerosol stream 162 irrespective of the attitude of a patient's head 150 or upper body. Use of a short delivery tube 20, such as 8-20 cm., enables the nebulizer 30 to be suspended to one side of a patient's head and remain in a vertical attitude. With a longer delivery tube, the nebulizer may be suspended to the side of a body support such as a gurney or bed, not shown.

Continuing in FIG. 4, second conduit means 130 of the CPAP apparatus 100 has a first end 131A connected through outlet 126 to an exemplary diluter 106. The second end 131B of the second conduit means 130 is shown connected to the second Tee fitting port 14. The third Tee fitting port 18 is shown connected to the mask inhalation port 112, for mixing and simultaneous continuous injection of a pressurized oxygenation gas 158 and an aerosol 162 of medication 160 into a CPAP mask 110. The mask 110 is configured to maintain a continuous positive pressure in the patient's airway.

Turning now to FIG. 5, individual elements of an exemplary medication delivery device 10 of the invention are shown in an exploded view. These elements include a Tee fitting 12 with first port 16, second port 14 and third port 18. Ports 14 and 18 are shown as having common centerline 46, while second port 14 intercepts centerline 46 at a preferred angle 48 of 90 degrees. Another angle 48 such as e.g. 30 degrees or 45 degrees may be used. In FIG. 5, the second port 14 of the Tee fitting 12 is typically a male port which fits into second conduit means 130, and the third port of Tee fitting 12 is typically a female port which accepts the male inhalation port 112 of the mask 110. The Tee fitting 12 may be formed to include an internal orifice, not shown, of reduced diameter for increasing the velocity of CPAP gas 158 (decreasing the pressure thereof) past the entering nebulized aerosol stream 162, thus drawing the aerosol into the CPAP gas and enhancing mixing.

In FIG. 5, a medicinal delivery tube 20 is shown with an outlet end 24 connectable to port 16 of the Tee fitting 12 by direct connection. Aerosol delivery tube 20 has sufficient flexibility to readily form a bend to a vertical orientation within a small length of tube 20, in order to make the nebulizer 30 orientation independent of the patient's position. Thus, for example, a readily available corrugated plastic tubular material of nominal 1-2 cm. ID will bend at least 180 degrees within a length of about 10-20 cm. under the suspended weight of a conventional small nebulizer 30 used by emergency teams. However, tubing which will bend through at least 120 degrees in the same length may also be used. A conventional nebulizer in widespread use weighs about one ounce (28 g). Thus, the best tube material available will readily support a nebulizer 30 in a vertical position, regardless of the attitude of a patient's head. The delivery tube 20 is typically formed of a short length of a flexible corrugated plastic tubing of a smaller diameter than the diameter of the second conduit means 130. Preferably, the aerosol delivery tube 20 has a diameter about one-half that of the CPAP oxygen supply tube 130. An example of a tubing which works well as a delivery tube 20 is a nominal ½ inch (1.27 cm.) outside diameter corrugated tubing formed of polyethylene, available from Carodyne, which has a place of business in Indianapolis, Ind. The medication delivery apparatus of the invention, including nebulizer 30, adapter 22, delivery tube 20 and Tee fitting 12 may weigh as little as about 2 ounces (56 grams) or less.

As shown, the tube inlet end 22 of the delivery tube 20 is attachable to the gas port outlet 34 of nebulizer 30, either through adapter 42, or by direct connection to the outlet 34.

Nebulizer 30 may be of any construction useful in the medical field. For use in emergency vehicles and the like, where space is limited, it is preferable to stock as few types of equipment as possible; so a single type of nebulizer is preferably used to satisfy all or most of the needs. For use in this invention, it is required that the nebulizer be constructed for suspension from a medication delivery tube 20 in an orientation which permits the desired maximum continuous nebulization of medication 160. Refilling or exchange of a nebulizer 30 is readily accomplished during CPAP operation. Exchange of a nebulizer is possible in a short time, i.e. seconds. The inlet gas port 32 of nebulizer 30 is connectable to a source of oxygen-containing gas by an intervening gas supply tube 36. The pressure and flow rate of oxygen/air are controlled by means known in the art to provide the desired aerosolization rate. Such pressure and flow controlling means may be further incorporated into a BiPAP/CPAP machine, so that the CPAP gas 158 and nebulizer gas 162 have independently controlled pressures and flow rates. Lightweight plastic nebulizers useful in the present invention are commercially available, and together with connected tubing are intended to be disposable after use by a patient.

As shown in FIG. 6, a Tee fitting 12 may be connected in an alternate configuration where the aerosol 162 is introduced into a port 14 or 18 other than the side port 16 of the Tee fitting. The 3-port fitting 12 may also comprise a Y fitting or in fact have ports 14, 16 and 18 at any angle 48 to each other, provided ready connection/disconnection and rapid delivery of the aerosol are achieved.

Figure 7:
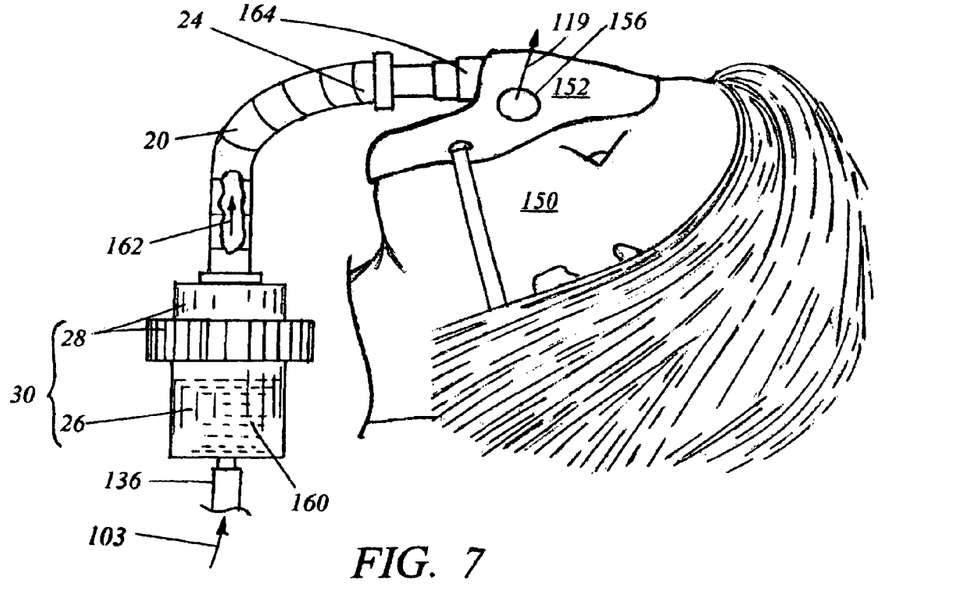
FIG. 7 is a perspective view of a medication delivery device of the invention connected to a conventional nebulizer face mask worn by a supine patient.

Turning now to FIG. 7, a secondary use of the medication dosing apparatus 10 of the invention is illustrated. Simple supply of a medicinal aerosol 162 and oxygen to a patient may be conducted despite a prone position of a patient's head 150. As shown in this figure, a non-CPAP (non-pressurized) mask 152 has an inlet port 164 and vents 156 through which exhalate 119 is vented. Despite the generally horizontal orientation of the inlet port 164, the nebulizer 30 is maintained in a non-spilling vertical orientation for efficient nebulization of liquid medication 160 to an aerosol by a stream of gas, e.g. oxygen or air from source 102.

As already indicated, methods of the invention avoid problems in administering medication aerosols in emergency situations, and result in added comfort to the patient, avoidance of endotracheal intubation, enhanced control of nebulization over a wide range of rates, generally higher nebulization rates, and decreased work load for the attending EMT's.

The present invention has been described in specific embodiments intended in all respects to be illustrative rather than limiting in natue. It is to be understood that the invention defined by the appended claims is not to be limited by specific details set forth in the above description and that alternative embodiments will become apparent to those of ordinary skill in the art to which the invention pertains without departing from the spirit and scope thereof.

What is claimed is:

1. An aerosol delivery device for delivering an aerosol to a CPAP-treated patient in an emergency vehicle in a substantially continuous flow of oxygen-enriched air in a CPAP apparatus continuously maintained at a pressure greater than atmospheric, comprising:

an emergency CPAP apparatus for establishing and maintaining an open airway in a patient;

a nebulizer having upper and lower ends, comprising:
 a container for liquid;
 a nebulizer inlet for introducing a pressurized gas for aerosolizing said liquid;
 a nebulizer outlet at said upper end of said nebulizer for discharging said aerosol at an elevated pressure;

a flexible aerosol delivery tube with an inlet end connected to said nebulizer outlet for receiving said aerosol, and an outlet end;

a three-port tubular Tee fitting having a first port connectable to said outlet end of said flexible aerosol delivery tube for receiving said aerosol therefrom, and second and third ports;

an elongate gas supply tube connectable to said second port of said tubular Tee fitting for supplying a continuous flow of oxygen-containing gas thereto to mix with said aerosol at a desired controllable elevated pressure;

a face mask for delivery of said mixture of oxygen-containing gas and aerosol to a patient's mouth and nose at a continuously maintained positive pressure, said mask having an inlet connectable to said third port of said tubular three port Tee fitting for receiving said continuously pressurized mixture of oxygen-containing gas and aerosol in a substantially continuous stream; and a face mask outlet for controllable discharge of mask contents, with settable pressure control means for setting and continuously maintaining said desired elevated pressure at a value within a range of between about 1 and about 100 cm. water in said mask;

wherein said aerosol delivery tube has a length whereby said nebulizer is suspended downwardly therefrom and maintained in a generally vertical attitude to maintain said aerosol delivery during CPAP operation.

2. An aerosol delivery device in accordance with claim 1, wherein said liquid in said nebulizer comprises an aerosolizable medicinal material.

3. An aerosol delivery device in accordance with claim 1, wherein said flexible delivery tube comprises a corrugated plastic tube having a diameter less than the diameter of said gas supply tube.

4. An aerosol delivery device in accordance with claim 1, wherein said flexible delivery tube has a diameter of about one-half of the diameter of said gas supply tube.

5. An aerosol delivery device in accordance with claim 1, wherein said flexible delivery tube is bendable up to at least about 180 degrees while suspendingly supporting said nebulizer in a generally vertical position.

6. An aerosol delivery device in accordance with claim 1, wherein said flexible delivery tube is bendable up to at least about 120 degrees while suspendingly supporting said nebulizer in a generally vertical position.

7. An aerosol delivery device in accordance with claim 1, wherein said flexible delivery tube maintains said nebulizer in a vertical position irrespective of the attitude of said face mask.

8. An aerosol delivery device in accordance with claim 1, wherein said flexible delivery tube has a length of between about 5 cm. and about 100 cm.

9. An aerosol delivery device in accordance with claim 1, wherein said flexible delivery tube has a length of between about 10 cm and about 50 cm.

10. An aerosol delivery device in accordance with claim 1, wherein said flexible delivery tube has a length of between about 10 cm. and about 30 cm.

11. An aerosol delivery device in accordance with claim 1, wherein said flexible delivery tube comprises flexible plastic tubing having an inside diameter of about 5 mm to about 25 mm.

12. An aerosol delivery device in accordance with claim 1, wherein said flexible delivery tube comprises flexible plastic tubing having an inside diameter of about 5 mm to about 15 mm.

13. An aerosol delivery device in accordance with claim 1, wherein said flexible delivery tube comprises corrugated plastic tubing.

14. An aerosol delivery device according to claim 1, wherein said pressure control means is capable of being set to maintain a mask pressure at a value within a range of about 1-25 cm. water.

15. An aerosol delivery device according to claim 1, wherein said pressure control means is capable of being set to maintain a mask pressure at a value within a range of about 2.5-12.5 cm. water.

\* \* \* \* \*